United States Patent [19]

Messmer et al.

[11] 4,324,786
[45] Apr. 13, 1982

[54] PYRIDO[2,3-e]-AS-TRIAZINE DERIVATIVES AND PHARMACEUTICAL COMPOSITIONS

[75] Inventors: András Messmer; Pál Benkő; György Hajós; Lujza Petőcz; Ibolya Kosóczky; Péter Görög, all of Budapest, Hungary

[73] Assignee: Egyt Gyogyszervegyeszeti Gyar, Budapest, Hungary

[21] Appl. No.: 143,778

[22] Filed: Apr. 25, 1980

[30] Foreign Application Priority Data

Apr. 28, 1979 [HU] Hungary ............................. EE 2654

[51] Int. Cl.³ .................. A61K 31/535; A61K 31/53; C07O 471/04
[52] U.S. Cl. .............................. 424/248.54; 424/249; 544/112; 544/184
[58] Field of Search ............................. 544/112, 184; 424/248.54, 249

[56] References Cited

U.S. PATENT DOCUMENTS 3,108,102 10/1960 Carbon ................................. 544/184
3,137,693 6/1964 Carbon ................................. 544/184

OTHER PUBLICATIONS

Hauptmann et al., Chem. Abstracts, vol. 86 (1977) No. 89768c.

*Primary Examiner*—Henry R. Jiles
*Assistant Examiner*—R. W. Ramsuer
*Attorney, Agent, or Firm*—Young & Thompson

[57] ABSTRACT

New pyrido[2,3-e]-as-triazine derivatives of the general formula (I),

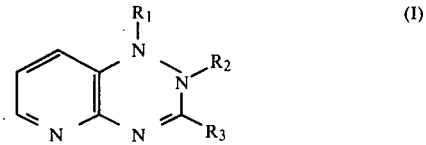

wherein
$R^1$ and $R^2$ each stand for a $C_{1-20}$ alkylcarbonyl, halogenated ($C_{1-4}$ alkyl)-carbonyl, $C_{1-4}$ alkoxycarbonyl, benzoyl, phenyl-($C_{1-4}$ alkyl)-carbonyl or phenyl-($C_{2-4}$ alkenyl)-carbonyl group or a 5-10-membered mono- or bicyclic nitrogen-containing heterocyclic acid residue (preferably a pyridylcarbonyl group) containing optionally one or more additional nitrogen, oxygen and/or sulfur atoms in the heterocyclic ring, and optionally one or more identical or different substituents selected from the group consisting of halogen, $C_{1-4}$ alkoxy, nitro and hydroxy are attached to the aromatic or heterocyclic rings, furthermore one of $R^1$ and $R^2$ may also stand for hydrogen atom, or $R^1$ and $R^2$ may form, together with the adjacent nitrogen atoms, a pyrazole-2,4 ring having optionally a $C_{1-6}$ alkyl substituent in position 3, and $R^3$ stands for hydrogen, halogen, $C_{1-4}$ alkoxy, amino, mono-($C_{1-6}$ alkyl)-amino, di-($C_{1-6}$ alkyl)-amino, hydroxy, alkylated or acylated hydroxy, morpholino, piperazino, N-($C_{1-6}$ alkyl)-piperazino, N-benzylpiperazino or N-pyridylpiperazino group, and pharmaceutically acceptable acid addition salts thereof are prepared by acylating the respective 1,2-unsubstituted 1,2-dihydro-pyrido[2,3-e]-as-triazine derivatives.

The new compounds according to the invention act on the central nervous system and exert sedative, analgesic, narcosis potentiating, tetrabenazine antagonizing and antiphlogistic effects. The new compounds according to the invention can be applied to advantage in the therapy.

5 Claims, No Drawings

PYRIDO[2,3-e]-AS-TRIAZINE DERIVATIVES AND PHARMACEUTICAL COMPOSITIONS

The invention relates to new pyrido[2,3-e]-as-triazine derivatives and pharmaceutical compositions containing the same.

The new pyrido[2,3-e]-as-triazine derivatives according to the invention correspond to the general formula (I),

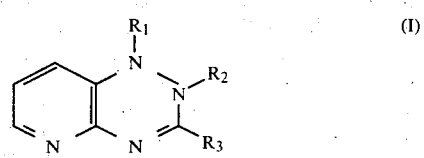

wherein $R^1$ and $R^2$ each stand for a $C_{1-20}$ alkylcarbonyl, halogenated ($C_{1-4}$ alkyl)-carbonyl, $C_{1-4}$ alkoxycarbonyl, benzoyl, phenyl-($C_{1-4}$ alkyl)-carbonyl or phenyl-($C_{2-4}$ alkenyl)-carbonyl group or a 5-10-membered mono- or bicyclic nitrogen-containing heterocyclic acid residue (preferably a pyridylcarbonyl group), containing optionally one or more additional nitrogen, oxygen and/or sulfur atoms in the heterocyclic ring, and optionally one or more identical or different substituents selected from the group consisting of halogen, $C_{1-4}$ alkoxy, nitro and hydroxy, are attached to the aromatic or heterocyclic rings, furthermore one of $R^1$ and $R^2$ may also stand for hydrogen, or $R^1$ and $R^2$ may form, together with the adjacent nitrogen atoms, a pyrazole-3,5-dione ring having optionally a $C_{1-6}$ alkyl substituent in position 4, and $R^3$ stands for hydrogen, halogen, $C_{1-4}$ alkoxy, amino, mono-($C_{1-6}$ alkyl)-amino, di-($C_{1-6}$ alkyl)-amino, hydroxy, alkylated or acylated hydroxy, morpholino, piperazino, N-($C_{1-6}$ alkyl)-piperazino, N-benzylpiperazino or N-pyridylpiperazino group or $C_{1-4}$ alkoxycarbonyloxy-group.

The pharmaceutically acceptable acid addition salts of the above compounds are also embraced by the scope of the invention.

Preferred representatives of the new compounds having the general formula (I) are those wherein $R^1$ stands for acetyl, propionyl, chloroacetyl, benzoyl, phenylacetyl, phenylpropionyl, cinnamoyl, nicotinoyl, methoxycarbonyl or ethoxycarbonyl group, $R^2$ represents hydrogen or an acetyl, propionyl or benzoyl group, and $R^3$ stands for hydrogen, chlorine hydroxy, methoxy, diethylamino, di-(n-propyl)-amino, morpholino, N-benzylpiperazino, methoxycarbonyloxy or ethoxycarbonyloxy group, as well as the pharmaceutically acceptable acid addition salts of these compounds.

Particularly preferred representatives of the new compounds according to the invention are 3-morpholino-1,2-dipropionyl-1,2-dihydro-pyrido[2,3-e]-as-triazine and 3-diisopropylamino-1-propionyl-1,2-dihydro-pyrido[2,3-e]-as-triazine, as well as the pharmaceutically acceptable acid addition salts thereof.

The term "alkyl group", whenever used alone or in combination (such as alkoxy, alkylcarbonyl, etc.), refers to straight-chained or branched, saturated aliphatic hydrocarbyl groups. The $C_{1-20}$ alkylcarbonyl group may be e.g. an acetyl, propionyl, butyryl, stearinyl, etc. group. Of the halo-($C_{1-4}$ alkyl)-carbonyl groups e.g. chloroacetyl, bromoacetyl, chloropropionyl, etc. groups can be mentioned as preferred representatives. The $C_{1-4}$ alkoxycarbonyl group may be e.g. methoxycarbonyl, ethoxycarbonyl, n-propoxycarbonyl, etc. Of the phenyl-($C_{1-4}$ alkyl)-carbonyl groups e.g. the phenylacetyl, $\beta$-phenylpropionyl and $\alpha$-phenylpropionyl groups are to be mentioned. An example of the preferred phenyl($C_{2-4}$ alkenyl)-carbonyl groups is the cinnamoyl group. The heterocyclic moiety of the 5 to 10-membered, mono- or bicyclic heterocyclic acid residue containing a nitrogen atom optionally together with one or more additional nitrogen, oxygen and/or sulfur heteroatoms may be e.g. a furyl, pyridyl, thienyl, pyrrolyl, imidazolyl, pyrazolyl, pyrazinyl, pyrimidinyl, pyridazinyl, quinolyl, isoquinolyl, benzimidazolyl, benzothiazolyl, benzisothiazolyl etc. group. The aromatic or heterocyclic rings of the aromatic or heterocyclic acyl groups may have optionally one or more identical or different substituents. Of the substituents the halogen atoms (e.g. chlorine, bromine), alkoxy groups (e.g. methoxy, ethoxy, n-propoxy, etc.), furthermore the nitro and hydroxy groups are to be mentioned. The term "halogen atom" covers all the four halogens, i.e. fluorine, chlorine, bromine and iodine.

The pharmaceutically acceptable acid addition salts of the compounds having the general formula (I) are those formed with mineral or organic acids conventionally applied for salt formation, such as hydrochloric, hydrobromic, sulfuric, nitric, phosphoric, lactic, succinic, maleic, fumaric, malic, tartaric, etc. acids.

For the preparation of a compound having the general formula (I) or a pharmaceutically acceptable acid addition salt thereof, a compound of the general formula (II),

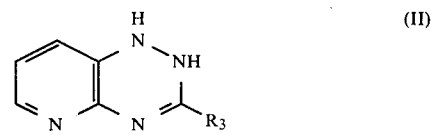

wherein $R^3$ is as defined above, or a salt thereof is reacted with an acylating agent of the general formula (III) or (IV),

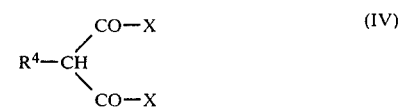

wherein $R^1$ is as defined above, $R^4$ stands for hydrogen or a $C_{1-6}$ alkyl group and X is a leaving group, and, if desired, a resulting compound of the general formula (I), wherein $R^3$ is hydroxy, is alkylated or acylated in a manner known per se, a resulting diacyl compound of the general formula (I) is converted into the respective monoacyl derivative by partial hydrolysis, and/or a free base of the general formula (I) is converted into its pharmaceutically acceptable acid addition salt, or is liberated from its salt.

The starting substances of the general formula (II) can be prepared by reduction from the respective pyrido-as-triazine derivatives disclosed in the U.S. Pat. Nos. 3,108,102 and 3,137,693. The acylating agents of the general formulae (III) and (IV) can be prepared as described in Houben-Weyl: Methoden der präp. org. Chemie 11/2, pp. 10–14, 16–19 and 31–34.

The starting substances of the general formula (II) can be utilized as free bases or in the form of their salts. Of the salts e.g. those formed with common mineral or organic acids (e.g. hydrochloric, hydrobromic, fumaric, tartaric, etc. acids) can be applied. In the compounds of the general formulae (III) and (IV) X is an appropriate leaving group. Preferred acylating agents of the general formulae (III) and (IV) are those wherein X stands for halogen, particularly chlorine (acyl halides, particularly chlorides), $C_{1-4}$ alkoxy group (esters), hydroxy group (free acids) or $C_{1-4}$ alkanoyloxy group (symmetrical or mixed anhydrides). All acylating agents corresponding to the general formulae (III) and (IV) capable of acylating a secondary amine can be applied in the process of the invention.

The reaction can be performed in a solvent. As reaction medium e.g. halogenated hydrocarbons (such as methylene chloride, chloroform, etc.), aromatic hydrocarbons (such as xylene, toluene, benzene), various ethers (such as diethyl ether, tetrahydrofuran, dioxane, etc.), mixtures of hydrocarbons (such as petrol), aliphatic or aromatic carboxylic acids and mixtures of the above solvents can be applied. The reaction can be performed at temperatures of 10° to 180° C., preferably at 30° to 140° C. The reaction is conducted preferably under an inert gas atmosphere (e.g. nitrogen, argon, etc.).

According to a preferred method 1 to 10 molar equivalents of an acylating agent of the general formula (III) or (IV) are dissolved or suspended in an appropriate inert solvent, thereafter a solution or a suspension of one molar equivalent of a compound having the general formula (II) is added, and, if necessary, the reaction mixture is placed under an inert gas atmosphere. When a carboxylic anhydride or an ester is applied as acylating agent, the reaction is performed preferably at 40° to 140° C., particularly preferably at the boiling point of the reaction mixture, and when a carbonyl halide is utilized, the reaction can be conducted at lower temperatures. During the progress of the reaction the starting substances usually dissolve in the reaction medium to form a homogeneous or almost homogeneous mixture, and then the crystals of the end-product start to separate. The product can be isolated and, if desired, purified by methods known per se.

When a malonic acid derivative of the general formula (IV) is applied as acylating agent, the reaction is performed preferably under an inert gas atmosphere (e.g. nitrogen or argon).

When a free acid of the general formula (III), i.e. a compound wherein X is hydroxy, is applied as acylating agent, the reaction is performed preferably in the presence of a usual condensing agent, such as dicyclohexyl carbodiimide. When a functional derivative, particularly a halide, of a carboxylic acid is applied as acylating agent, it is preferable to add an acid binding agent, e.g. an alkali carbonate, alkali hydrocarbonate, alkali hydroxide or an organic amine (such as sodium or potassium carbonate, sodium or potassium hydrocarbonate, sodium or potassium hydroxide, triethylamine, dimethylamine, pyridine, etc.), to the reaction mixture. The acid binding agent is applied preferably in less than equimolar amounts. The type of the acid binding agent applied has no significant effect on the yield or the feasibility of the reaction.

If an acylating agent of the general formula (III) is applied, depending on the structure of the acylating agent and the nature of the substituent attached to position 3 of the starting pyrido[2,3-e]-as-triazine derivative, mono- or diacyl compounds of the general formula (I) can be prepared.

On the other hand, if a compound of the general formula (IV) is applied as acylating agent, compounds of the general formula (I) are obtained, wherein $R^1$ and $R^2$, together with the adjacent nitrogen atoms, form a pyrazole-2,4-dione ring having optionally a $C_{1-6}$ alkyl substituent (e.g. a methyl, ethyl, n-propyl, isopropyl, n-hexyl, n-butyl, etc. group) in position 3. This latter alkyl group corresponds to substituent $R^4$ of the acylating agent having the general formula (IV). The resulting compounds, formed in a single step, contain the new pyrazolo[1,2-a]pyrido[2,3-e]-as-triazine ring system.

The compounds of the general formulae (Ia) and (Ib),

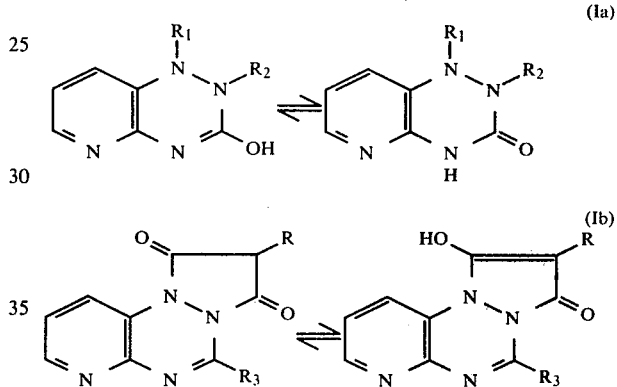

wherein R stands for hydrogen or a $C_{1-6}$ alkyl group, represent a special subgroup of the pyrido[2,3-e]-as-triazine derivatives of the general formula (I). In these compounds $R^3$ is always a hydroxy group, and in those of the general formula (Ib) a pyrazole-diode ring is fused with the as-triazine ring. As it follows from the chemical structures, these compounds may also be present in enolic form, i.e. there is a keto-enol tautomeric equilibrium. In other words, this process varient may yield 1-oxo-3-ol, 1-ol-3-oxo or 1,3-diol derivatives or various mixtures thereof as endproducts. Since these reactions generally yield both tautomeric forms of the compounds which can sometimes not be separated, the invention embraces all the possible isomers and isomeric mixtures of these compounds as well as the processes yielding any isomer or isomeric mixture.

The diacyl derivatives of the general formula (I), wherein both $R^1$ and $R^2$ stand for acyl group, can be converted by partial hydrolysis into the respective monoacyl compounds of the general formula (I), wherein one of $R^1$ and $R^2$ stands for acyl and the other is hydrogen. Preferred representatives of the monoacyl compounds are those in which $R^1$ is acyl and $R^2$ is hydrogen. The partial hydrolysis can be performed in a manner known per se, by reacting the diacyl derivative with an alkali (e.g. an alkali hydroxide, carbonate or hydrocarbonate).

Compounds of the general formula (I) in which $R^3$ is hydroxy can be alkylated or acylated to obtain derivatives in which $R^3$ is an alkylated or acylated hydroxy group. Alkylation and acylation can be performed in a manner known per se, with commonly used reactants capable of alkylating or acylating a hydroxy group.

The compounds of the general formula (I) are basic in character, and they can be converted into pharmaceutically acceptable acid addition salts by methods well known in the art. One can proceed e.g. by reacting a free base of the general formula (I) with an equimolar amount of the selected acid in an appropriate solvent. The bases can be liberated from their salts by conventional methods.

The new pyrido[2,3-e]-as-triazine derivatives of the general formula (I) and their pharmaceutically acceptable acid addition salts have important therapeutical properties. In particular, they act on the central nervous system, and exert sedative, analgesic, narcosis potentiating, tetrabenazine antagonizing and antiphlogistic effects. These compounds can be applied to advantage in the therapy. It is a further advantage of the new compounds according to the invention that they exert their biological effects in any form of administration (e.g. when administered orally or injected intramuscularly, intravenously or subcutaneously).

The invention relates further to pharmaceutical compositions containing as active agent at least one compound of the general formula (I) or a pharmaceutically acceptable acid addition salt thereof, together with a conventional inert, solid or liquid pharmaceutical carrier. The pharmaceutical compositions may be solid, semisolid or liquid preparations, such as tablets, coated tablets, capsules, suppositories, solutions, suspensions, emulsions, etc., suitable for enteral or parenteral administration. The unit dosages of orally administerable preparations contain preferably about 5 to 200 mg of the active agent.

Tablets, coated tablets, capsules and other solid pharmaceutical compositions may contain conventional pharmaceutical carriers and/or additives, such as binding agents (e.g. tragacanth gum, starch, gelatine, dipotassium phosphate, etc.), disintegrating agents (e.g. starch, alginic acid), lubricants (e.g. magnesium stearate), sweetening agents (e.g. sucrose, lactose, saccharine), flavouring agents (e.g. pepper), etc.

The injectable pharmaceutical compositions, such as sterile solutions or dispersions, may contain e.g. water, ethanol, polyols (such as glycerol, liquid polyethylene glycols, propylene glycol and mixtures thereof), vegetable oils, etc. as liquid component.

The pharmaceutical compositions of the invention may also contain other conventional additives and/or auxiliary agents, if necessary.

The daily oral dosage of the new compounds having the general formula (I) is usually 50 to 1200 mg. These limits are, however, only approximate since, depending on the age, body weight and general health conditions of the patient, the activity of the compound applied and the prescriptions of the physician, higher or lower amounts can be administered as well.

The biological effects of the new compounds according to the invention are demonstrated by the results of the following pharmacological tests, performed according to standard methods.

The toxicity was determined on mice after oral adminstration. The $LD_{50}$ values of the substances tested are given in Table 1.

TABLE 1

| Toxicity | |
|---|---|
| Compound (No. of Example) | $LD_{50}$ mg/kg |
| 1 | 1600 |
| 2 | 2000 |
| Meprobamate | 1100 |
| Amitryptiline | 225 |
| Paracetamol | 510 |
| Phenylbutazone | 1000 |
| Acetylsalicylic acid | 1500 |

The motility inhibiting effects of the new compounds were tested on mice by the method of Borsy et al. [Int. Pharmacodyn. 124, 1-2 (1960)]. The compounds to be tested were administered orally to the animals. The results are given in Table 2.

TABLE 2

| Motility inhibiting effect | | |
|---|---|---|
| Compound (No. of Example) | $ED_{50}$ mg/kg | Therapeutical index |
| 1 | 320 | 5 |
| 2 | 250 | 8 |
| Meprobamate | 270 | 4.1 |

The narcosis potentiating effects was tested on mice according to the method of Kaergaard [Arch. Int. Pharmacodyn. 2, 170 (1967)]. The compounds under examination were administered orally to the animals. The results are given in Table 3.

TABLE 3

| Narcosis potentiating effect | | |
|---|---|---|
| Compound (No. of Example) | $ED_{50}$ mg/kg | Therapeutical index |
| 1 | 54 | 29.6 |
| 2 | 40 | 50 |
| Meprobamate | 250 | 4.2 |

The ability of the compounds in inhibiting the ptosis provoked by tetrabenazine was determined on mice after oral administration, as described by Brodie [Psychopharmacologia 2, 467 (1963)]. The results are given in Table 4.

TABLE 4

| Tetrabenazine antagonizing effect | | |
|---|---|---|
| Compound (No. of Example) | $ED_{50}$ mg/kg | Therapeutical index |
| 1 | 320 | 5 |
| 2 | 150 | 13.3 |

The ability of the compounds in potentiating the toxicity of yohimbine was tested on mice by the method of Quinton [Brit. J. Pharmacol. 21, 51 (1963)]. The compounds were administered orally to the animals. The results are given in Table 5.

TABLE 5

| Potentiation of the toxicity of yohimbine | | |
|---|---|---|
| Compound (No. of Example) | $ED_{50}$ mg/kg | Therapeutical index |
| 1 | 320 | 5 |
| 2 | 140 | 14.3 |

The analgesic effects of the new compounds were tested on mice after oral administration, as described by Newbould [Brit. J. Pharmacol. 35, 487 (1969)]. The results are given in Table 6.

TABLE 6

| Compound (No. of Example) | Analgesic effect ED$_{50}$ mg/kg | Therapeutical index |
|---|---|---|
| 1 | 300 | 5.3 |
| 2 | 350 | 5.7 |
| Paracetamol | 180 | 2.8 |

The antiphlogistic effects of the new compounds were determined on rats by the method of Winter [Proc. Soc. Exp. Biol. Med. 111, 544 (1962)]. The compounds were administered orally to the animals. The results are given in Table 7.

TABLE 7

| Compound (No. of Example | Antiphlogistic effect ED$_{50}$ mg/kg | Therapeutical index |
|---|---|---|
| 1 | 300 | 5.3 |
| 2 | 450 | 4.4 |

The invention is elucidated in detail by the aid of the following non-limiting Examples.

EXAMPLE 1

Preparation of 3-morpholino-1,2-dipropionyl-1,2-dihydro-pyrido[2,3-e]-as-triazine A mixture of 3.0 g (0.01 moles) of 3-morpholino-1,2-dihydro-pyrido[2,3-e]-as-triazine-dihydrochloride and 40 ml of propionic anhydride is heated at 125° C. for 2 hours. The resulting deep yellow solution is cooled and admixed with ether. The separated precipitate is filtered off, stirred with saturated aqueous sodium carbonate solution and, if necessary, recrystallized from ethanol. 1.5 g (58%) of the title compound are obtained; m.p.: 173°–174° C.

Analysis: calculated N%=21.0; found N%=21.05
Molecular weight: 331.

EXAMPLE 2

Preparation of 3-diisopropylamino-1-propionyl-1,2-dihydro-pyrido[2,3-e]-as-triazine A mixture of 5.0 g (0.021 moles) of 3-diisopropylamino-1,2-dihydro-pyrido[2,3-e]-as-triazine and 40 ml of propionic anhydride is heated at 120° C. under argon atmosphere. After 2 hours of heating the mixture is cooled, the separated crystalline product is filtered off, the crystals are dissolved in chloroform, and the solution is filtered through a column filled with silica gel. The effluent is evaporated to obtain 3.5 g (57%) of the title compound; m.p.: 199°–200° C.

Analysis: calculated N%=24.20; found N%=24.22
Molecular weight: 325.

EXAMPLE 3

Preparation of 3-chloro-1-propionyl-1,2-dihydro-pyrido[2,3-e]-as-triazine

A mixture of 8.0 g (0.048 moles) of 3-chloro-1,2-dihydro-pyrido[2,3-e]-as-triazine and 60 ml of propionic anhydride is heated at 120° C. for 30 minutes under argon atmosphere. A homogeneous solution forms, and the crystals of the end-product soon start to separate. After 1 hour the crystals are filtered off. 6.8 g (64%) of the title compound are obtained; m.p.: 205°–206° C.

Analysis: calculated N%=24.94; found N%=24.63
Molecular weight: 224.

EXAMPLE 4

Preparation of 3-methoxy-1-propionyl-1,2-dihydro-pyrido[2,3-e]-as-triazine

A mixture of 4.5 g (0.027 moles) of 3-methoxy-1,2-dihydro-pyrido[2,3-e]-as-triazine, 25 ml of propionic anhydride and 25 ml of propionic acid is heated at 100° to 120° C. under argon temperature. The reaction mixture is allowed to cool and the separated crystals are filtered off. 4.5 g (75%) of the title compound are obtained; m.p.: 197°–198° C.

Analysis: calculated N%=25.44 found N%=25.29
Molecular weight: 220.

EXAMPLE 5

Preparation of 3-hydroxy-1,2-dipropionyl-1,2-dihydro-pyrido[2,3-e]-as-triazine 2.0 g (0.013 moles) of 3-hydroxy-1,2-dihydro-pyrido[2,3-e]-as-triazine are reacted with 16 ml of propionic anhydride as described in Example 3 to obtain 2.45 g (72%) of the title compound; m.p.: 186°–187° C.

Analysis: calculated N%=21.36 found N%=21.29
Molecular weight: 262.

EXAMPLE 6

Preparation of 1-phenylacetyl-3-hydroxy-1,2-dihydropyrido[2,3-e]-as-triazine

A mixture of 2.5 g (0.016 moles) of 3-hydroxy-1,2-dihydro-pyrido[2,3-e]-as-triazine, 3.5 ml (5.8 g, 0.038 moles) of phenylacetyl chloride and 50 ml of dry acetonitrile is heated at 60° C. for one hour under argon atmosphere. The reaction mixture is cooled and the separated product is filtered off. 2.8 g (63%) of the title compound are obtained; m.p.: 220°–221° C.

Analysis: calculated N%=20.88 found N%=20.95
Molecular weight: 268.

EXAMPLE 7

Preparation of 3-hydroxy-1-cinnamoyl-1,2-dihydro-pyrido[2,3-e]-as-triazine 7.5 g (0.05 moles) of 3-hydroxy-1,2-dihydro-pyrido[2,3-e]-as-triazine are reacted with 17 g (0.102 moles) of cinnamoyl chloride in 150 ml of acetonitrile as described in Example 6. 9.0 g (65%) of the title compound are obtained; m.p.: 221°–223° C.

Analysis: calculated N%=20.00 found N%=20.20
Molecular weight: 280.

EXAMPLE 8

Preparation of 1,2-dibenzoyl-3-hydroxy-1,2-dihydro-pyrido[2,3-e]-as-triazine

One proceeds as described in Example 6 with the difference that benzoyl chloride is applied instead of phenylacetyl chloride. The title compound, melting at 198°–199° C., is obtained with a yield of 91%.

EXAMPLE 9

Preparation of 1,2-dichloroacetyl-3-hydroxy-1,2-dihydro-pyrido[2,3-e]-as-triazine One proceeds as described in Example 6 with the difference that dichloroacetyl chloride is applied instead of phenylacetyl chloride. The title compound, melting at 210°–211° C., is obtained with a yield of 58%.

EXAMPLE 10

Preparation of 1,2-diacetyl-3-hydroxy-1,2-dihydro-pyrido[2,3-e]-as-triazine

3-Hydroxy-1,2-dihydro-pyrido[2,3-e]-as-triazine is reacted with acetic anhydride as described in Example 3. The title compound, melting at 149°–150° C., is obtained with a yield of 79.5%.

EXAMPLE 11

Preparation of 1-nicotinoyl-3-(N-benzylpiperazino)-1,2-dihydro-pyrido[2,3-e]-as-triazine hydrochloride 3-(N-Benzylpiperazino)-1,2-dihydro-pyrido[2,3-e]-as-triazine hydrochloride is reacted with nicotinoyl chloride as described in Example 6. The title compound, melting at 218°–219° C., is obtained with a yield of 83%.

EXAMPLE 12

Preparation of 1-methoxycarbonyl-3-methoxycarbonyloxy-1,2-dihydro-pyrido[2,3-e]-as-triazine hydrochloride A mixture of 2.5 g (0.015 moles) of 3-hydroxy-1,2-dihydro-pyrido[2,3-e]-as-triazine, 2.16 g (0.03 moles) of methyl chloroformate and 100 ml of dioxane is maintained at 5°–10° C. for 3 hours and then at 40°–50° C. for 5 hours. Thereafter the solvent is removed to obtain 3.58 g (79%) of the title compound; m.p.: 159°–160° C.

What we claim is:

1. A pyrido[2,3-e]-as-triazine derivative of the general formula (I),

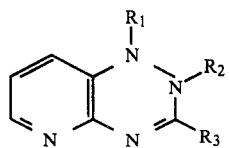

wherein $R^1$ and $R^2$ each stand for a $C_{1-20}$ alkylcarbonyl, halogenated ($C_{1-4}$ alkyl)-carbonyl, $C_{1-4}$ alkoxycarbonyl, benzoyl, phenyl-($C_{1-4}$ alkyl)-carbonyl or phenyl-($C_{2-4}$ alkenyl)-carbonyl group or a 5–10 membered mono- or bicyclic nitrogen-containing heterocyclic acid residue (preferably a pyridylcarbonyl group) containing optionally one or more additional nitrogen, oxygen and/or sulfur atoms in the heterocyclic ring, and optionally one or more identical or different substituents selected from the group consisting of halogen, $C_{1-4}$ alkoxy, nitro and hydroxy, are attached to the aromatic or heterocyclic rings, furthermore one of $R^1$ and $R^2$ may also stand for hydrogen atom, or $R^1$ and $R^2$ form, together with the adjacent nitrogen atoms, a pyrazole-3,5-dione ring having optionally a $C_{1-6}$ alkyl substituent in position 4, and $R^3$ stands for hydrogen, halogen, $C_{1-4}$ alkoxy, amino, mono-($C_{1-6}$ alkyl)-amino, di-($C_{1-6}$ alkyl)-amino, hydroxy, alkylated or acylated hydroxy, morpholino, piperazino, N-($C_{1-6}$ alkyl)-piperazino, N-benzylpiperazino or N-pyridylpiperazino group or $C_{1-4}$ alkoxycarbonyloxy-group, or a pharmaceutically acceptable acid addition salt thereof.

2. A compound of the general formula (I), wherein $R^1$ stands for acetyl, propionyl, chloroacetyl, benzoyl, phenylacetyl, phenylpropionyl, cinnamoyl, nicotinoyl, methoxycarbonyl or ethoxycarbonyl group, $R^2$ represents hydrogen or an acetyl, propionyl or benzoyl group, and $R^3$ stands for hydrogen, chlorine, hydroxy, methoxy, diethylamino, di-(n-propyl)amino, morpholino, N-benzylpiperazino, methoxycarbonyloxy or ethoxycarbonyloxy group, or a pharmaceutically acceptable acid addition salt thereof.

3. 3-Morpholino-1,2-dipropionyl-1,2-dihydro-pyrido[2,3-e]-as-triazine, 3-diisopropylamino-1-propionyl-1,2-dihydro-pyrido[2,3-e]-as-triazine, or a pharmaceutically acceptable acid addition salt thereof.

4. Hydrochlorides of the compounds defined in claim 1.

5. A pharmaceutical composition comprising as active ingredient an effective amount of at least one pyrido[2,3-e]-as-triazine derivative of the general formula (I), wherein $R^1$, $R^2$ and $R^3$ are as defined in claim 1, or a pharmaceutically acceptable acid addition salt thereof together with a pharmaceutical carrier.

* * * * *